US009661990B2

(12) United States Patent
Hofer

(10) Patent No.: US 9,661,990 B2
(45) Date of Patent: May 30, 2017

(54) ENDOSCOPE AND METHOD FOR RECORDING AT LEAST ONE STEREOSCOPIC IMAGE BY MEANS OF AN ENDOSCOPE

(75) Inventor: Axel Hofer, Endingen (DE)

(73) Assignee: SCHOLLY FIBEROPTIC GMBH, Denzlingen (DE)

( * ) Notice: Subject to any disclaimer, the term of this patent is extended or adjusted under 35 U.S.C. 154(b) by 227 days.

(21) Appl. No.: 13/992,505

(22) PCT Filed: Nov. 30, 2011

(86) PCT No.: PCT/EP2011/005995
§ 371 (c)(1),
(2), (4) Date: Jun. 7, 2013

(87) PCT Pub. No.: WO2012/076128
PCT Pub. Date: Jun. 14, 2012

(65) Prior Publication Data
US 2013/0250061 A1     Sep. 26, 2013

(30) Foreign Application Priority Data
Dec. 9, 2010   (DE) .................. 10 2010 053 881

(51) Int. Cl.
| G02B 21/22 | (2006.01) |
| A61B 1/00 | (2006.01) |
| A61B 1/05 | (2006.01) |
| G02B 23/24 | (2006.01) |

(52) U.S. Cl.
CPC ...... *A61B 1/00193* (2013.01); *A61B 1/00096* (2013.01); *A61B 1/05* (2013.01); *G02B 23/243* (2013.01); *G02B 23/2415* (2013.01)

(58) Field of Classification Search
CPC . G03B 21/28; A61B 1/00193; A61B 1/00183; A61B 1/041; A61B 1/042; A61B 1/043; A61B 5/0084; A61B 1/0005; A61B 1/00096; A61B 1/05; A61B 1/055; G02B 26/0841; G02B 21/0048; G02B 21/22; G02B 21/0028; G02B 21/362; G02B 23/2415
USPC ....... 359/362, 363, 368, 369, 372, 373, 374, 359/375, 376, 377, 434, 435, 196, 197, 359/200, 212, 213, 214, 223, 226; 600/101, 109, 160, 166, 173, 175, 182
See application file for complete search history.

(56) References Cited

U.S. PATENT DOCUMENTS

| 4,862,873 A | 9/1989 | Yajima et al. | |
| 6,464,363 B1 * | 10/2002 | Nishioka et al. | ............. 359/846 |
| 6,627,987 B1 * | 9/2003 | Glenn et al. | .................. 257/704 |

(Continued)

FOREIGN PATENT DOCUMENTS

| DE | 3818104 | 12/1988 |
| JP | 63210813 | 9/1988 |

(Continued)

*Primary Examiner* — Scott J Sugarman
*Assistant Examiner* — Balram Parbadia
(74) *Attorney, Agent, or Firm* — Volpe and Koenig, P.C.

(57) ABSTRACT

An endoscope (1) is provided in which a mechanically or electrically adjustable mirror (7) is interposed between two lenses (3, 4) adapted for stereoscopic image recording and an image recording chip (5), the mirror allows light captured by the lenses (3, 4) to be alternately guided onto the image recording chip (5).

16 Claims, 4 Drawing Sheets

(56) References Cited

U.S. PATENT DOCUMENTS

| | | |
|---|---|---|
| 6,762,862 B2 * | 7/2004 | Lam et al. .................... 358/482 |
| 2001/0015847 A1 | 8/2001 | Sugawara |
| 2002/0118453 A1 * | 8/2002 | Geier et al. ................... 359/465 |
| 2002/0131139 A1 * | 9/2002 | Mandella ........... A61B 1/00183 359/214.1 |
| 2007/0188603 A1 * | 8/2007 | Riederer et al. ................ 348/54 |
| 2011/0285965 A1 * | 11/2011 | Sugiyama ...................... 353/10 |

FOREIGN PATENT DOCUMENTS

| | | |
|---|---|---|
| KR | 20070071791 | 7/2007 |
| WO | 2010047463 | 4/2010 |

* cited by examiner

ENDOSCOPE AND METHOD FOR RECORDING AT LEAST ONE STEREOSCOPIC IMAGE BY MEANS OF AN ENDOSCOPE

BACKGROUND

The invention relates to an endoscope having two lenses formed at a distal end, said lenses being arranged offset with respect to one another for recording a stereoscopic image, and having an image recording chip, which is configured for electronically recording images captured by the lenses, wherein a mirror, movable between a first position and a second position, is provided in the distal end region, wherein, in the first position, an image captured by a first lens of the two lenses can be conducted onto the image recording chip and, in the second position, an image captured by a second lens of the two lenses can be conducted onto the image recording chip.

The invention furthermore relates to a method for recording at least one stereoscopic image by means of an endoscope.

In order to evaluate the images captured by the two lenses, previous proposals suggested guiding the optical beam paths through the endoscope tube and evaluating them separately at the proximal end.

Alternative proposals suggested using one image recording chip for both lenses, wherein different recording regions of the image recording chip are employed for respectively one lens. Here, each lens respectively only uses half of the recording surface of the image recording chip, which is disadvantageous in terms of the achievable image resolution.

There has also been a proposal to develop a prism which unifies the beam paths downstream of the lenses and which, by means of polarizable attachments—so-called optical or electronic shutters—is configured in such a way that the various beam paths can be switched off separately from one another. However, it was found that the use of such shutters leads to an undesirable reduction in the conducted luminous energy.

SUMMARY

The invention is based on the object of improving arrangements of stereoscopic lenses in endoscopes.

In order to achieve this object, provision is, according to the invention, made in an endoscope of the type mentioned at the outset for respectively one deflection prism to be arranged behind each lens in the beam direction, by means of which deflection prism the image captured by the respective lens can be deflected onto the mirror, and for the deflection prisms to be formed on an integral prism body. Arranging the image recording chip in the distal end region provides the advantage that the beam paths required for image capture can be formed to be as short as possible. Hence, a desired flexibility of the endoscope can be achieved in the remaining sections in a simple fashion. The use of an adjustable mirror on the one hand offers the advantage of being able to employ the recording surface of the image recording chip in an optimum fashion for both images of the stereoscopic image and on the other hand offers the advantage of the luminous energy passing along the beam path being attenuated as little as possible. It is therefore possible to provide an endoscope which can provide high resolution and high quality images while having small dimensions.

An advantage arising when using deflection prisms is that it is possible to obtain a comparatively short length dimension.

A particularly compact design is achievable as a result of the fact that the deflection prisms are formed on an integral prism body. Moreover, the assembly of the endoscope is simplified since fewer components have to be assembled individually.

A simple mechanical arrangement arises if the mirror is suspended in a pivotable fashion. As a result, the mirror can be moved between the positions by pivoting.

In one embodiment of the invention, provision can be made for an actuation apparatus, by means of which the mirror can be adjusted electrically. Here, it is advantageous that the mirror can be adjusted in a very compact space. It is furthermore advantageous that the current position of the mirror can easily be synchronized with a downstream image processing unit, for example in order to enable the assignment of the right-hand and left-hand images of the stereoscopic image in a simple fashion.

By way of example, the mirror can be embodied as a DLP-mirror. DLP-mirrors (microsystems also known as DMD-mirrors [digital micro-mirror device mirrors]) are known per se, for example for use in beamers, and are distinguished by small spatial requirements and by reliable mechanical functional properties.

In one embodiment of the invention, provision can be made for the mirror to be suspended in a holding frame. Hence, the pivoting movement of the mirror can be guided in a simple fashion.

In one embodiment of the invention, provision can be made for the mirror and the holding frame to be integrally connected. It is furthermore advantageous that a mechanically robust suspension of the mirror can be provided.

In one embodiment of the invention, provision can be made for the mirror and the holding frame to be cut to size from a flat material. The production can thus be simplified. It is furthermore advantageous in this case that the spatial requirements can be minimized.

In one embodiment of the invention, provision can be made for the holding frame of the mirror to be attached to the prism body. It is advantageous in this case that the mirror can be inserted into the endoscope together with the prism body in a common production step. It is furthermore advantageous that the mirror, in the assembled position thereof, can be automatically aligned or alignable in relation to the deflection mirrors.

It is particularly expedient if the mirror can be pivoted in the case of an elastic deformation of a connecting web between the mirror and the holding frame or a holding frame. In this case, it is advantageous that a mechanically robust suspension is created. By way of example, provision can be made for the pivoting of the mirror to be able to be brought about by means of switchable electrostatic fields. To this end, corresponding field generators of the actuation apparatus or an actuation apparatus of the mirror can be formed, which exert an electrostatic or electromagnetic force onto the mirror and thus pivot the latter between the aforementioned two positions.

In one embodiment of the invention, provision can be made for the prism body to have a passage opening, through which beam paths are deflected from the lenses onto the image recording chip. The result of this is particularly compact beam guidance and the prism body can be supported by a sleeve or a wall of the endoscope.

A particularly stable embodiment can provide for the prism body to have an annular design and form a passage opening or the passage opening. In a further embodiment, the prism body can have an open or interrupted design on a circumferential section of the annular shape.

In one embodiment of the invention, provision can be made for the prism body to be a single crystal. It is advantageous in this case that the deflection prisms can be formed in a simple fashion. By way of example, the prism body can be made from a wafer with a corresponding thickness.

For manufacturing which can be reproduced particularly well, provision can be made for the prism body to be produced from a single crystal block by an etching process. It is advantageous in this case that the external geometry of the prism body can be defined and manufactured in a simple fashion.

It is particularly expedient if the deflection prisms respectively have a preferably planar reflection surface. In this case, provision can be made for the reflection surfaces respectively to lie in a crystal plane of the prism body. It is advantageous here that the angle at which the beam path from the respective lens is incident on the deflection prism and the reflection surface can easily be prescribed by the crystal geometry. What can, in a simple and reproducible fashion, be achieved by this is that the reflection surface has defined angles in relation to the external geometry of the prism body. Moreover, the reflection surfaces can easily be formed in the prism body by etching. Compared to convex or concave reflection surfaces, for example compared to hollow mirrors, flat reflection surfaces offer the advantage of aberrations being largely avoidable.

By way of example, it is possible to obtain a length dimension that is as short as possible by virtue of the fact that the reflecting surface of the mirror is formed on the side of the mirror facing away from the lenses. In this case, the deflection prisms can be configured in such a way that the light rays respectively incident from the lenses are cast back at the deflection prisms. This can result in a Z-shaped beam path.

For the purposes of a further space-saving embodiment, provision can be made for the mirror to be suspended from the prism body.

In order to be able to employ the image recording chip in an optimum fashion for each image, provision can be made for the mirror to illuminate, i.e. completely or at least substantially completely fill, the recording region of the image recording chip in each of the two positions.

In one embodiment of the invention, provision can be made for at least one lens element to be arranged in the beam path between the mirror and the image recording chip. By using a lens element, the beam path can easily be widened or focused in such a way that the recording region of the image recording chip is illuminated. This can be used for reducing the required installation length. It is particularly expedient for the lens element to be embodied as magnification lens element. Hence the recording region of the image recording chip can easily be illuminated with an otherwise tightly guided beam path.

In order to be able to penetrate very small openings without detriment to the image quality of image resolution, provision can be made for the distal end region to have a cross section which is determined by the dimensions of the image recording chip. The cross section is preferably dimensioned in such a way that the image recording chip just fits into the cross section.

Simple optical geometries emerge if the image recording chip is arranged with its recording region looking in the longitudinal direction of the endoscope. Hence the sensor surface is aligned perpendicular to the longitudinal direction.

In order to achieve the object, the invention provides, in the method mentioned at the outset, for a mirror, arranged in an end region of the endoscope, to be mechanically adjusted between a first position and a second position, wherein, in the first position, an image captured by a first lens and reflected by a first reflection surface of a prism body is deflected onto an image recording chip arranged in a distal end of the endoscope and, in the second position, an image captured by a second lens and reflected by a second reflection surface of the prism body is deflected onto the image recording chip, and for the image recording chip to record images when the mirror is positioned in the first position and in the second position and provide said images for stereoscopic viewing. The mirror is preferably adjusted alternately between the two positions. The invention therefore provides a simple manageable method, by means of which images for stereoscopic view can be obtained with the highest possible image resolution and image quality in the smallest possible space. An optical throughput of the captured images from the distal end to the proximal end can be dispensed with. The images can be transmitted electronically, which can be achieved in a space-saving fashion.

In one embodiment of the invention, provision can be made for the mirror to be held integrally connected to a holding frame, wherein the change between the first position and the second position of the mirror is brought about under elastic deformation of a connecting element between the mirror and the holding frame.

A device according to the invention is preferably used in the method according to the invention.

BRIEF DESCRIPTION OF THE DRAWINGS

The invention will now be described in more detail on the basis of exemplary embodiments; however, it is not restricted to these exemplary embodiments. Further exemplary embodiments emerge from combining individual features or a number of features of the patent claims amongst themselves and/or with individual features or a number of features from the exemplary embodiments.

In detail.

DETAILED DESCRIPTION OF THE PREFERRED EMBODIMENTS

Figure 1:
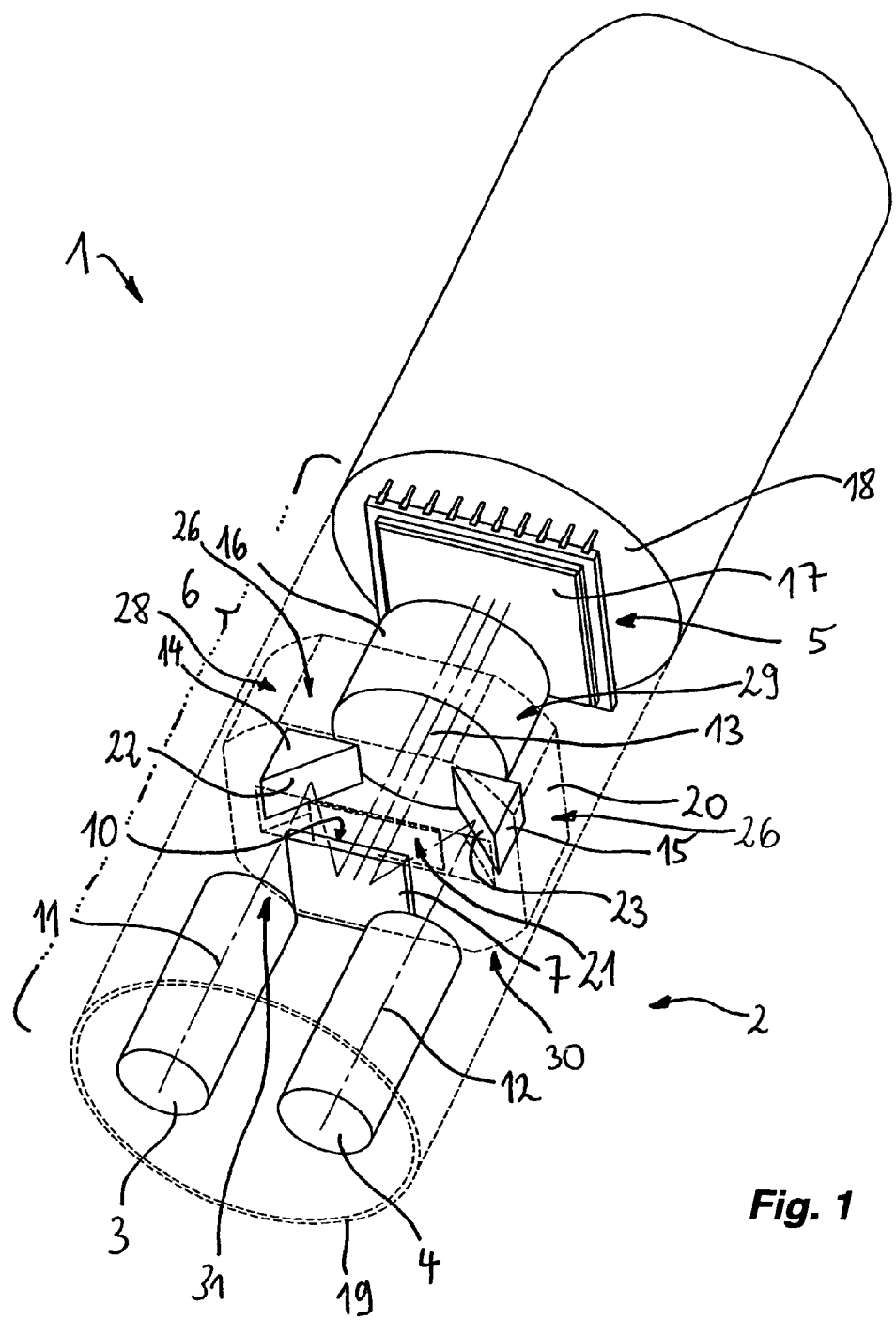
FIG. 1 shows an endoscope according to the invention in a three-dimensional perspective view.

The endoscope, which is shown in a schematic diagram in FIG. 1 and denoted in its entirety by 1, has a first lens 3 and a second lens 4 at its distal, i.e. facing away from the user, end 2. The lenses 3, 4 are arranged offset to one another and next to one another in a manner known per se for recording a stereoscopic image and capture a right-hand and a left-hand image.

The captured images are recorded electronically by an image recording chip 5. In order to be able to supply the right-hand and left-hand images to the image recording chip 5 in an alternating fashion, provision is made for a mirror 7 in the distal end region 6, which accommodates the lenses 3, 4 and the image recording chip 5.

Figure 2:
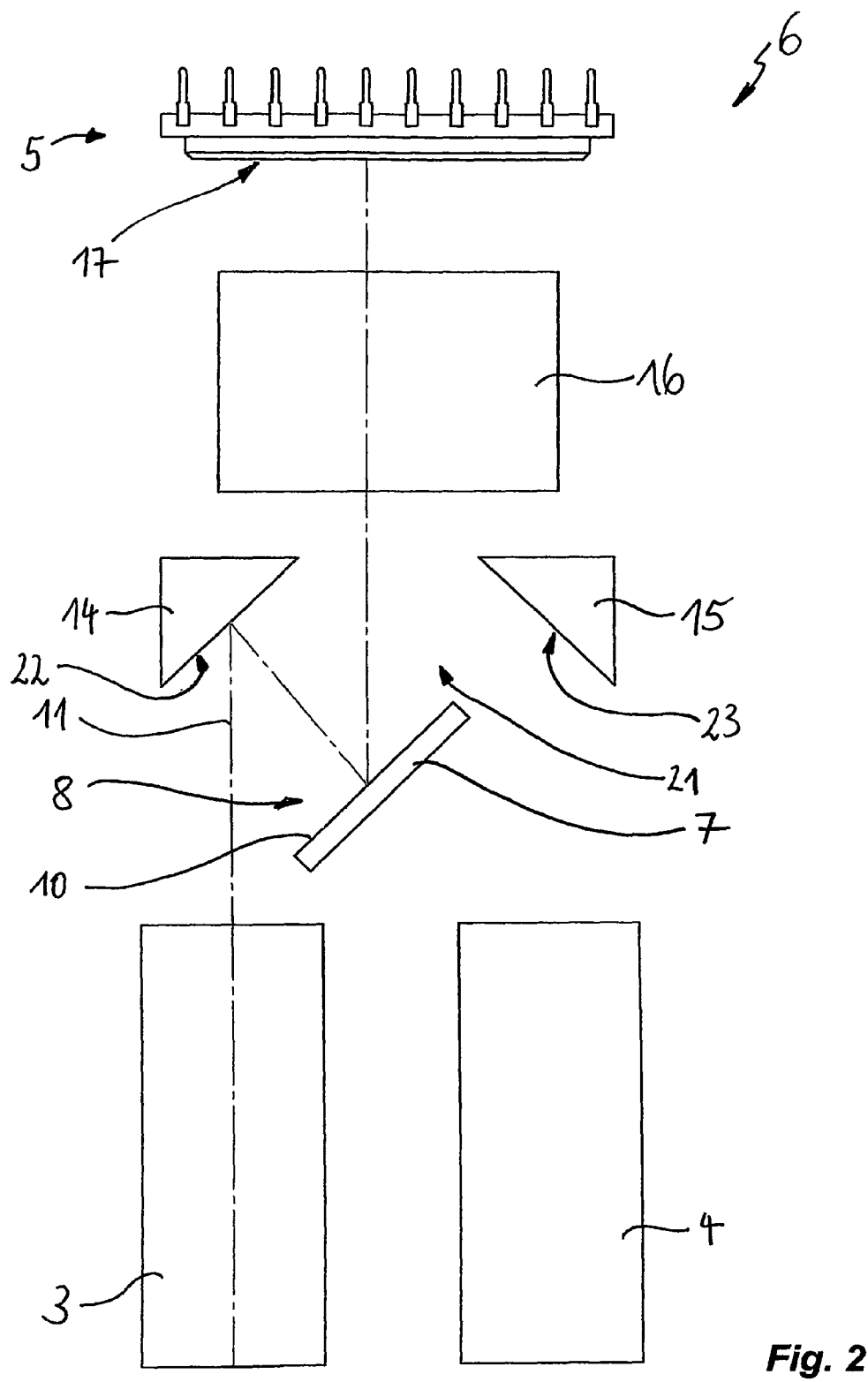
FIG. 2 shows a schematic diagram of the endoscope in accordance with FIG. 1, with the mirror in a first position.
Figure 3:
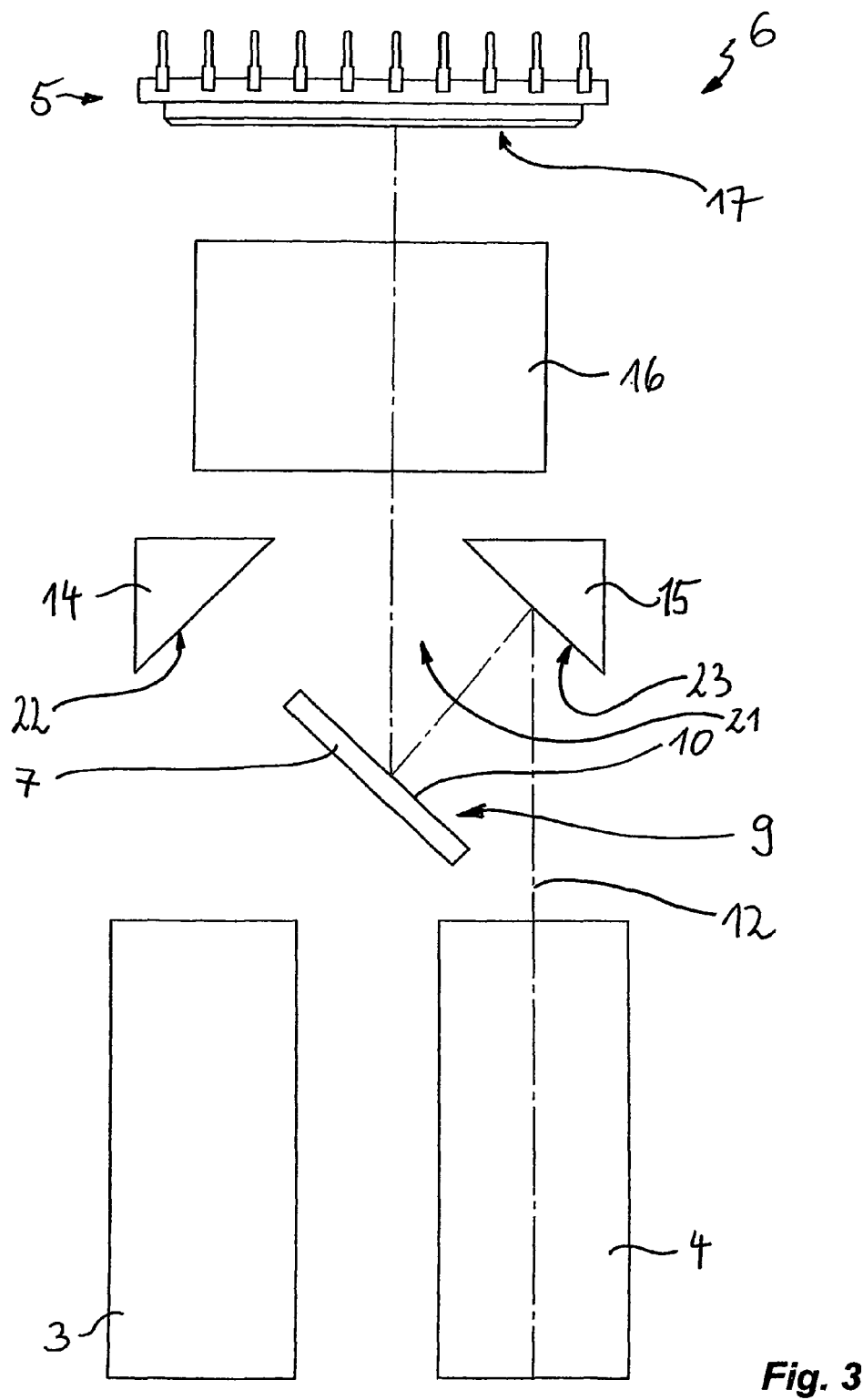
FIG. 3 shows the arrangement in accordance with FIG. 2, with the mirror in a second position.

FIG. 2 and FIG. 3 show, in a plan view, the components of the endoscope 1 according to the invention, which components are required to explain the functional principle and arranged in the distal end region 6. The remaining components, required in an endoscope 1, and the prism body 20, described below, have been omitted in order to simplify the illustration.

The mirror 7 is arranged such that it can be adjusted between a first position 8, which is shown in FIG. 2, and a second position 9 in accordance with FIG. 3.

In the exemplary embodiment, the mirror 7 is embodied as DLP-mirror and embodied in an electronically pivotable fashion. The details in this respect are known per se and have not been imaged here in order to simplify the illustration.

In the first position 8 in accordance with FIG. 2, the mirror 7 with its reflecting surface 10 forms a first beam path 11, by means of which an image captured by the first lens 3 can be conducted and is conducted onto the image recording chip 5 through the passage opening 21 of the prism body 20.

Hence, in the first position 8 of the mirror 7, the image recording chip 5 records a right-hand image via the first lens 3.

In the second position 9 of the mirror 7, cf. FIG. 3, the reflecting surface 10 defines a second beam path 12, via which the image captured by the second lens 4 can be conducted and is conducted onto the image recording chip 5 through the passage opening 21 of the prism body 20.

In the second position 9 of the mirror 7, the image recording chip 5 therefore receives a left-hand image via the second lens 4.

FIG. 1 shows the mirror in a central position, in which the surface normal 13 of the reflecting or mirrored surface 10 is aligned along the direction of extent of the distal end region 6 and faces away from the lenses 3, 4. In this position, no image is conducted onto the image recording chip 5 from the lenses 3, 4.

In order to obtain the Z-shaped course of the beam paths 11, 12, visible in FIG. 2 and FIG. 3, provision is made for deflection prisms 14, 15, which cast the respective rays arriving at the lenses 3, 4 back onto the mirror 7.

The deflection prisms 14, 15 are formed on a common prism body 20 and hence integrally connected.

The prism body 20 is pressed or cast as a glass body. It can also be polished or etched from a single crystal.

The deflection prisms 14, 15 respectively have one reflection surface 22, 23, at which the beam paths 11, 12 are reflected. The first beam path 11 of the image captured by the first lens 3 is therefore reflected at the first reflection surface 22 of the prism body 20, while the second beam path 12 of the image captured by the second lens 4 is reflected at the second reflection surface 23 of the prism body 20.

The prism body 20 surrounds a central passage opening in an annular fashion, through which passage opening the beam paths 3, 4 are guided onto the recording region 17 of the image recording chip 15.

The prism body 20 is formed with an external contour which fills the cross section 18 of the endoscope 1. Hence the prism body 20 is held directly by the sleeve 19.

A lens element 16—a positive lens element—is arranged between the mirror 7 and the image recording chip 5, which lens element widens or focuses the beam paths 11, 12 in such a way that the sensitive recording region 17 of the image recording chip 5 is illuminated.

In order to enable the largest possible recording region 17 in the case of the smallest possible dimensions of the endoscope 1 in the distal end region 6, the dimensions of the image recording chip 5 are fitted into the cross section 18 of the distal end section 6.

With its recording region 17, the image recording chip 5 looks at the lenses 3, 4 in the longitudinal direction of the distal end region 6.

A protective sleeve 19 or a protective tube surrounds the distal end region 6 or the whole endoscope 1. The external contour of the prism body 20 is matched to the cross section 18 of the endoscope in such a way that the rounded-off corners 28, 29, 30, 31 of the prism body 20, otherwise having a rectangular or square cross section transversely to the longitudinal axis of the endoscope 1, are fitted into the sleeve 19 or the tube.

In the exemplary embodiment shown in FIGS. 1 to 3, the lenses 3, 4 are formed separately from one another. In further exemplary embodiments, the lenses 3, 4 can also be formed on a common optical element. In this case, the lenses 3, 4 can consist of a common lens element.

In the exemplary embodiment in accordance with FIGS. 1 to 3, the deflection prisms 14 and 15 are be formed integrally on a common optical element—the prism body 20.

Figure 4:
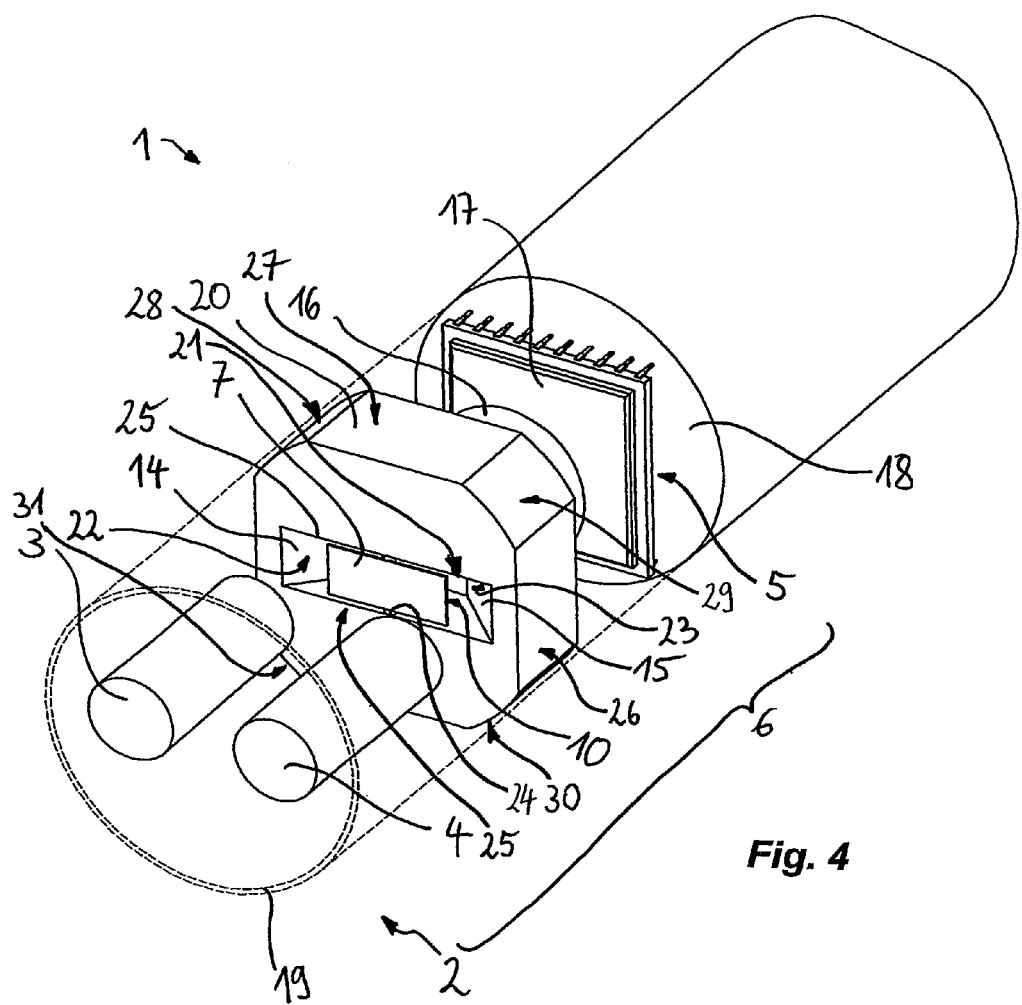
FIG. 4 shows a further endoscope according to the invention.

A further exemplary embodiment is shown in FIG. 4, in which components with the same function are denoted by the same reference sign as in FIGS. 1 to 3. The functional description provided there therefore also applies to this exemplary embodiment.

In the exemplary embodiment in accordance with FIG. 4, provision is likewise made for an integral prism body 20, on which the deflection prisms 14, 15 are formed.

The annular shape of the prism body 20, by means of which the passage opening 21 is surrounded, renders it possible to suspend the mirror 7 on the prism body 20 in such a way that the mirror 7 guides the beam paths 11, 12 onto the recording region 17 through the passage opening 21.

On two sides, the mirror 7 is integrally connected to a rectangular holding frame 25, which is merely indicated and not visible in any more detail, via connecting webs 24. The holding frame 25 extends around the passage opening 21 at the edge of the latter and is attached to the prism body 20 over a large surface. The mirror 7, the connecting webs 24 and the holding frame 25 are cut out of flat material.

The prism body 20 is etched out of a single crystal.

Here, the reflection surfaces 22, 23 are embodied in such a way that they respectively describe one crystal plane of the prism body 20.

Hence the reflection surfaces 22, 23 keep a defined angle in relation to the side surfaces 26, 27 and the remaining side surfaces of the prism body 20 if the side surfaces 26, 27 and the remaining side surfaces likewise describe crystal planes of the prism body 20. These angles are fixedly prescribed by the crystal structure of the single crystal and set during the etching process.

During operation of the endoscope 1, the mirror 7 is alternately pivoted between the positions 8, 9. In the process, the connecting webs 24 are deformed elastically. These connecting webs 24 therefore bring about a restoring force for the mirror 7 to return to the rest position as per FIG. 4. The image recording chip 5 is read-out synchronously thereto, and so left-hand and right-hand images are captured separately. These images are provided for stereoscopic viewing.

The deflection of the mirror 7 is brought about by electrostatic or electromagnetic fields, which are exerted onto the mirror of via an appropriate field generator (not illustrated in any more detail). Such switchable field generators for generating electrostatic or electromagnetic fields are known per se.

A proposal for the endoscope 1 provides that the mirror 7, which can be moved by mechanical or electrical means, is arranged between two lenses 3, 4 which are configured for stereoscopic image recording and an image recording chip 5, by means of which the light captured by the lenses 3, 4 can alternately be guided onto the image recording chip 5.

The invention claimed is:

1. An endoscope (1) comprising two lenses (3, 4) formed at a distal end (2), said lenses being arranged offset with respect to one another for recording a stereoscopic image, an image recording chip (5) configured for electronically recording images captured by the lenses (3, 4), a mirror (7), movable between a first position (8) and a second position (9), is provided in a distal end region (6), in the first position (8), an image captured by a first lens (3) of the two lenses (3, 4) is conducted onto the image recording chip (5) and, in the second position (9), an image captured by a second lens (4) of the two lenses (3, 4) is conducted onto the image recording chip (5), the image recording chip (5) is arranged in the distal end region (6), one deflection prism (14, 15) is arranged respectively behind each of the lenses (3, 4) in a beam direction, by said deflection prism the image captured by the respective lens (3, 4) is deflected onto the mirror (7) in the respective first or second position, and the deflection prisms (14, 15) are formed on an integral prism body (20), wherein the mirror (7) is a digital micromirror device mirror and is suspended in a pivotable fashion on the prism body (20), and wherein the deflection prisms (14, 15) each have one reflection surface (22, 23) at which beam paths (11, 12) are reflected and wherein the prism body (20) has a passage opening (21), through which the beam paths (11, 12) are deflected from the lenses (3, 4) to the image recording chip (5), or the prism body (20) has an annular design and forms a passage opening (21) through which the beam paths (11, 12) are deflected from the lenses (3, 4) to the image recording chip (5).

2. The endoscope (1) as claimed in claim 1, wherein an actuation apparatus is provided, by which the mirror (7) can be adjusted electrically.

3. The endoscope as claimed in claim 1, wherein the mirror (7) is suspended in a holding frame (25).

4. The endoscope of claim 3, wherein the mirror (7) and the holding frame (25) are integrally connected.

5. The endoscope of claim 3, wherein the mirror (7) and the holding frame (25) are cut to size from a flat material.

6. The endoscope of claim 3, wherein the holding frame (25) of the mirror (7) is attached to the prism body (20).

7. The endoscope as claimed in claim 1, wherein the mirror (7) is pivoted via an elastic deformation of a connecting web (24) between the mirror (7) and a holding frame (25) by switchable electrostatic fields.

8. The endoscope (1) as claimed in claim 1, wherein the prism body (20) is at least one of a single crystal or is produced from a single crystal block by an etching process.

9. The endoscope (1) as claimed in claim 1, wherein the mirror (7) illuminates the recording region (17) of the image recording chip (5) in each of the two positions (8, 9).

10. The endoscope (1) as claimed in claim 1, wherein the distal end region (6) has a cross section (18) which is determined by dimensions of the image recording chip (5).

11. The endoscope of claim 1, wherein the reflection surfaces (22, 23) of the deflection prisms (14, 15) are flat.

12. The endoscope of claim 1, wherein a magnification lens element is arranged in the beam path (11, 12) between the mirror (7) and the recording chip (5).

13. The endoscope of claim 1, wherein the two lenses are formed separately from one another.

14. A method for recording at least one stereoscopic image by an endoscope (1), wherein a -digital micromirror device mirror (7) is suspended in a pivotable fashion on a prism body (20), arranged in an end region (6) of the endoscope (1), the mirror (7) is mechanically moved between a first position (8) and a second position (9), the method comprising in the first position (8), capturing an image by a first lens (3) and reflecting the image by a first reflection surface (22) of a first deflection prism (14) of the prism body (20) so that the image is deflected onto an image recording chip (5) arranged in a distal end (2) of the endoscope (1) and, in the second position (9), capturing an image by a second lens (4) and reflecting the image by a second reflection surface (23) of a second deflection prism (15) of the prism body (20) so that the image is deflected onto the image recording chip (5) and the image recording chip (5) records images when the mirror (7) is positioned in the first position (8) and in the second position (9) and provides said images for stereoscopic viewing and wherein the prism body (20) has a passage opening (21), through which the beam paths (11, 12) are deflected from the lenses (3, 4) to the image recording chip (5), or the prism body (20) has an annular design and forms a passage opening (21) through which the beam paths (11, 12) are deflected from the lenses (3, 4) to the image recording chip (5).

15. The method as claimed in claim 14, wherein the mirror (7) is held integrally connected to a holding frame (25), a change between the first position and the second position of the mirror (7) is brought about via elastic deformation of a connecting element (24) between the mirror (7) and the holding frame (25).

16. An endoscope (1) comprising two lenses (3, 4) formed at a distal end (2), said lenses being arranged offset with respect to one another for recording a stereoscopic image, an image recording chip (5) configured for electronically recording images captured by the lenses (3, 4), a mirror (7), movable between a first position (8) and a second position (9), is provided in a distal end region (6), in the first position (8), an image captured by a first lens (3) of the two lenses (3, 4) is conducted onto the image recording chip (5) and, in the second position (9), an image captured by a second lens (4) of the two lenses (3, 4) is conducted onto the image recording chip (5), the image recording chip (5) is arranged in the distal end region (6), one deflection prism (14, 15) is arranged respectively behind each of the lenses (3, 4) in a beam direction, by said deflection prism the image captured by the respective lens (3, 4) is deflected onto the mirror (7) in the respective first or second position, and the deflection prisms (14, 15) are formed on an integral prism body (20), wherein the mirror (7) is a digital micromirror device mirror and is suspended in a pivotable fashion on the prism body (20), and wherein the deflection prisms (14, 15) each have one flat reflection surface (22, 23), wherein the reflection surfaces (22, 23) respectively lie in a crystal plane of the prism body (20) and wherein the prism body (20) has a passage opening (21), through which the beam paths (11, 12) are deflected from the lenses (3, 4) to the image recording chip (5), or the prism body (20) has an annular design and forms a passage opening (21) through which the beam paths (11, 12) are deflected from the lenses (3, 4) to the image recording chip (5).

* * * * *